United States Patent
Watabe et al.

(10) Patent No.: US 7,077,713 B2
(45) Date of Patent: Jul. 18, 2006

(54) ENGINE SPEED CONTROL SYSTEM FOR OUTBOARD MOTOR

(75) Inventors: Hiroshi Watabe, Wako (JP); Hideaki Takada, Wako (JP); Yoshinori Masubuchi, Wako (JP)

(73) Assignee: Honda Giken Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/669,716

(22) Filed: Sep. 25, 2003

(65) Prior Publication Data
US 2004/0065300 A1  Apr. 8, 2004

(30) Foreign Application Priority Data
Oct. 2, 2002  (JP) .............................. 2002-289942

(51) Int. Cl.
*B63H 21/21* (2006.01)

(52) U.S. Cl. ................. 440/1; 440/84; 440/87
(58) Field of Classification Search .................... 440/1, 440/84, 87
See application file for complete search history.

(56) References Cited

U.S. PATENT DOCUMENTS

| 5,809,436 | A  | * | 9/1998  | Gregory  | 701/21   |
|-----------|----|---|---------|----------|----------|
| 6,213,820 | B1 | * | 4/2001  | Kanno    | 440/1    |
| 6,294,988 | B1 | * | 9/2001  | Shomura  | 340/438  |
| 6,494,188 | B1 | * | 12/2002 | Kanno    | 123/491  |
| 6,679,205 | B1 | * | 1/2004  | Morikami | 123/90.15 |

FOREIGN PATENT DOCUMENTS

JP  2001-041079  2/2001

* cited by examiner

*Primary Examiner*—Sherman Basinger
(74) *Attorney, Agent, or Firm*—Westerman, Hattori, Daniels & Adrian, LLP

(57) ABSTRACT

In an engine speed control system for an outboard motor having a throttle valve that regulates air to be sucked and an actuator connected to the throttle valve to move it in an opening direction or in a closing direction, the actuator is driven to move the throttle valve in the closing direction such that the engine speed drops, if it is discriminated that a detected engine speed exceeds a predetermined speed (set to a speed at which the engine can assumably continue to run until the boat has returned to port), when a trouble has occurred in the engine. Thus, the system can lower the engine speed so as to allow the boat to return to port, without causing the engine to vibrate, when a trouble has occurred in the engine.

9 Claims, 5 Drawing Sheets

ENGINE SPEED CONTROL SYSTEM FOR OUTBOARD MOTOR

BACKGROUND OF THE INVENTION

1. Field of the Invention

This invention relates to an engine speed control system for an outboard motor.

2. Description of the Related Art

In an outboard motor to be used as a propulsion unit of boats, when a trouble such as overheating occurred in its internal combustion engine, the engine must continue to run until the boat has returned to port.

Aside from the above, in recent outboard motors, fuel injection or ignition is electronically controlled through an electronic control unit (ECU), although steering, throttling and shift-changing are still mechanically controlled using a cable or link. In such a type of the outboard motors, as taught in Japanese Laid-Open Patent Application No. 2001-41079, when a trouble has occurred in the engine (in the prior art, the trouble is a failure of sensor for sensing operating conditions of the engine), the ECU retards ignition timing, thins out the number of ignitions, or discontinues ignition at a certain cylinder if the engine is multi cylinder engine, so as to lower the engine speed such that the engine is protected from being damaged.

However, in the prior art, since the engine speed is lowered by retarding ignition timing or by decreasing the number of ignitions, the engine is likely to vibrate and this makes the operator feel unpleasant.

SUMMARY OF THE INVENTION

An object of the present invention is therefore to overcome the foregoing problems by providing an engine speed control system for an outboard motor that can lower the engine speed, without causing the engine to vibrate, when a trouble has occurred in the engine.

In order to achieve the foregoing object, this invention provides a system for controlling a speed of an internal combustion engine installed in an outboard motor mounted on a boat and having a propeller powered by the engine to propel the boat, the engine having a throttle valve that regulates air to be sucked, comprising: an actuator connected to the throttle valve to move it in an opening direction or in a closing direction; engine speed detecting means for detecting the speed of the engine; engine trouble detecting means for detecting a trouble occurred in the engine; engine speed discriminating means for discriminating whether the detected engine speed exceeds a predetermined speed when it is detected that the trouble has occurred in the engine; and actuator driving means for driving the actuator to move the throttle valve in the closing direction such that the engine speed drops, when it is discriminated that the detected engine speed exceeds the predetermined speed.

BRIEF DESCRIPTION OF THE DRAWINGS

The above and other objects and advantages of the invention will be more apparent from the following description and drawings, in which.

DETAILED DESCRIPTION OF THE PREFERRED EMBODIMENT

An engine speed control system for an outboard motor according to an embodiment of the present invention will now be explained with reference to the attached drawings.

Figure 1:
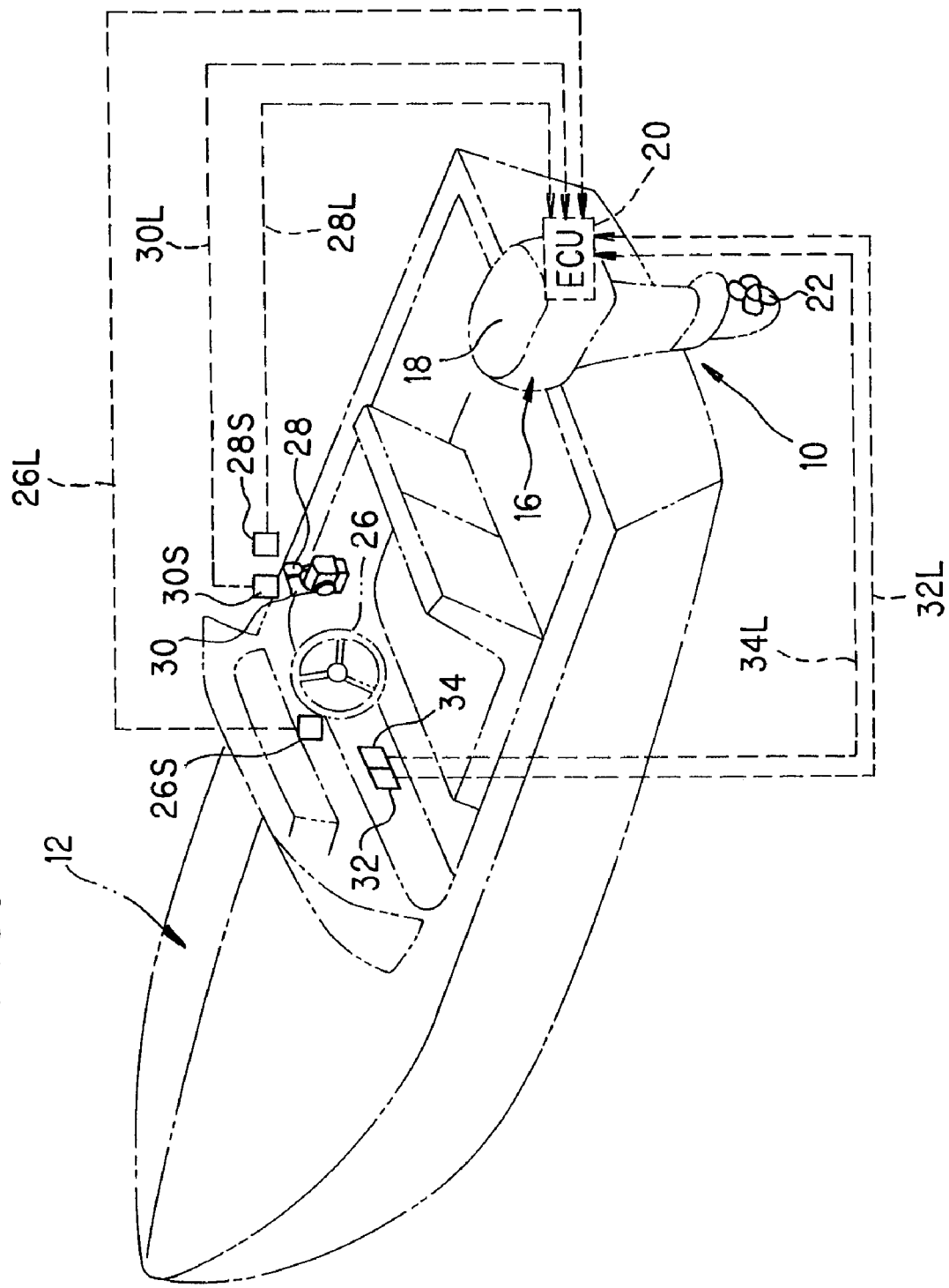
FIG. 1 is an overall schematic view of an engine speed control system for an outboard motor according to an embodiment of the invention.
Figure 2:
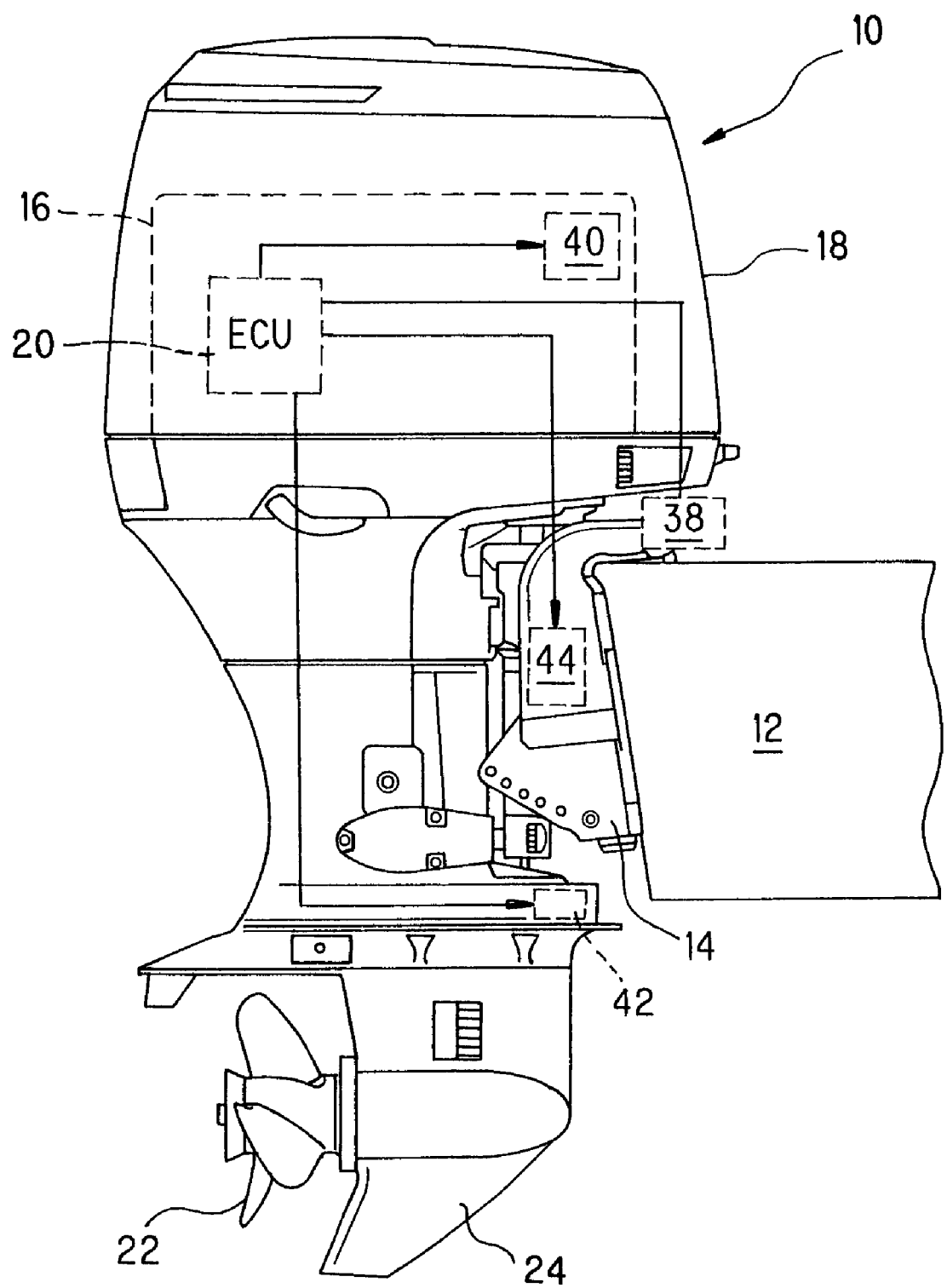
FIG. 2 is an explanatory side view of a part of FIG. 1.

FIG. 1 is an overall schematic view of the system with main focus on an outboard motor, and FIG. 2 is an explanatory side view of a part of FIG. 1.

Reference numeral 10 in FIGS. 1 and 2 designates an outboard motor built integrally of an internal combustion engine, propeller shaft, propeller and other components. The outboard motor 10 is mounted on the stern of a hull (boat) 12 via stem brackets 14 (shown in FIG. 2).

As shown in FIG. 2, an internal combustion engine 16 is installed at the upper portion (in the gravitational direction indicated) of the outboard motor 10. The engine 16 is a spark-ignition, V-type six-cylinder gasoline engine with a displacement of 2,200 cc. The engine 16, located inside the outboard motor 10, is enclosed by an engine cover 18 and positioned above the water surface. An electronic control unit (ECU) 20 constituted of a microcomputer is installed near the engine 16 enclosed by the engine cover 18.

The outboard motor 10 is equipped at its lower part with a propeller 22 and a rudder 24. The rudder 24 is fixed near the propeller 22 and does not rotate independently. The propeller 22, which operates to propel the boat 12 in the forward and reverse directions, is powered by the engine 16 through a crankshaft, drive shaft, gear mechanism and shift mechanism (none of which is shown), as will be explained later.

As shown in FIG. 1, a steering wheel 26 is installed near the operator's seat of the boat 12, and a steering angle sensor 26S installed near the steering wheel 26 outputs a signal in response to the turning of the steering wheel 26 by the operator. A throttle lever 28 is mounted on the right side of the operator's seat, and a throttle lever position sensor 28S installed near the throttle lever 28 outputs a signal in response to the position of the throttle lever 28 by the operator.

A shift lever 30 is mounted on the right side of the operator's seat near the throttle lever 28, and a shift lever position sensor 30S is installed near the shift lever 30 and outputs a signal in response to the position of the shift lever 30 by the operator. A power tilt switch 32 for regulating the tilt angle and a power trim switch 34 for regulating the trim angle of the outboard motor 10 are also installed near the operator's seat. These switches output signals in response to tilt up/down and trim up/down instructions input by the operator. The outputs of the steering angle sensor 26S, the throttle lever position sensor 28S, the shift lever position sensor 30S, the power tilt switch 32 and power trim switch 34 are sent to the ECU 20 over signal lines 26L, 28L, 30L, 32L and 34L.

In response to the output of the steering angle sensor 26S sent over the signal line 26L, the ECU 20 operates an electric motor 38 (for steering; shown in FIG. 2) to steer the outboard motor 10, i.e., change the direction of the propeller 22 and rudder 24, and thereby turn the boat 12 right or left. And, in response to the output of the throttle lever position sensor 28S sent over the signal line 28L, the ECU 20 operates an electric motor (for throttle) 40 (not shown in FIGS. 1 and 2) to move the throttle valve and regulate the amount of air to be sucked into the engine 16.

Further, in response to the output of the shift lever position sensor 30S sent over the signal line 30L, the ECU 20 operates an electric motor (for shift-changing) 42 to change the rotational direction of the propeller 22 or cut off the transmission of engine power to the propeller 22. Moreover, in response to the outputs of the power tilt switch 32 and power trim switch 34 sent over the signal lines 32L, 34L, the ECU 20 operates a conventional power tilt-trim unit 44 to regulate the tilt angle and trim angle of the outboard motor 10.

Figure 3:
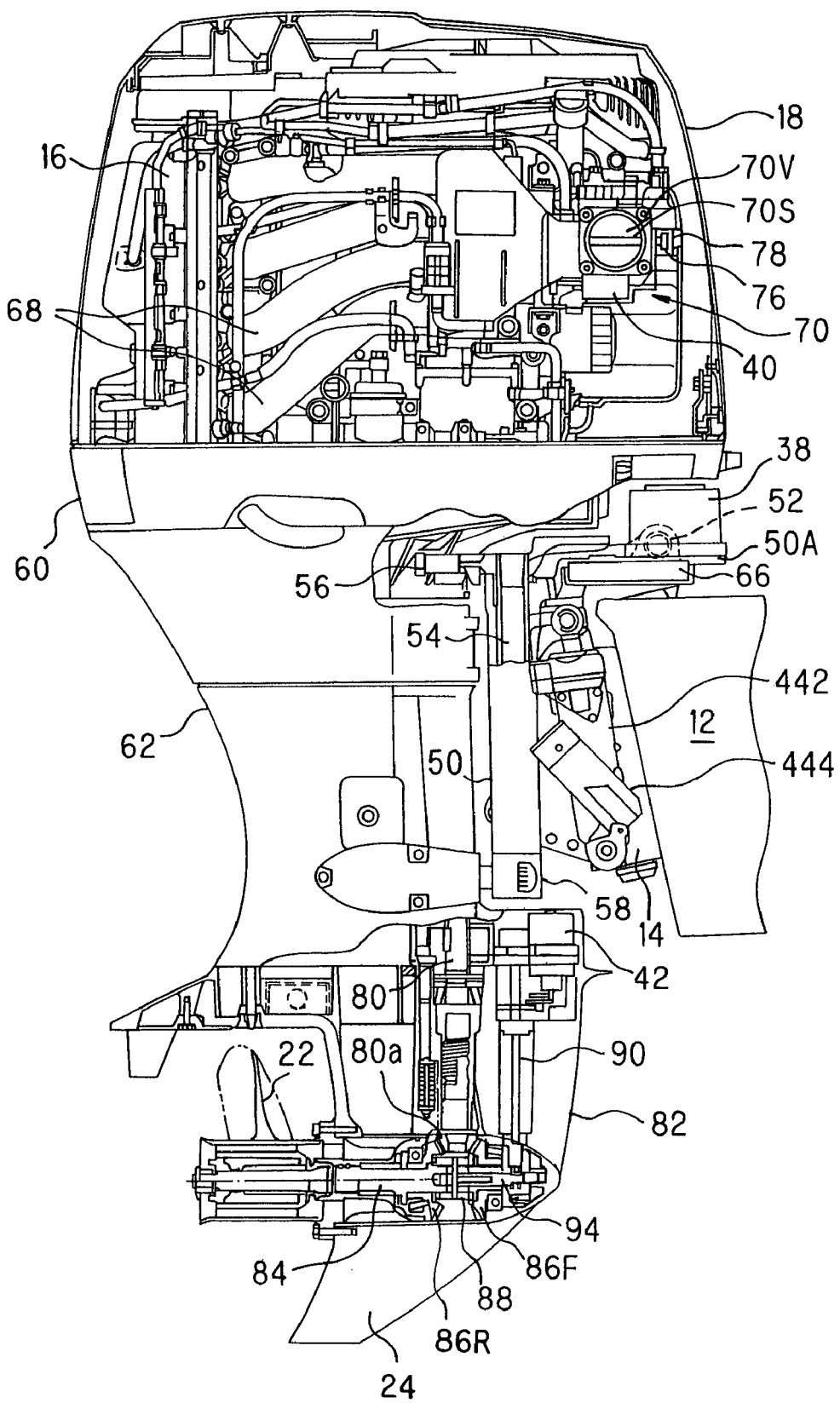
FIG. 3 is an enlarged explanatory side view of FIG. 2.

FIG. 3 is an enlarged explanatory side view. While this is basically an enlargement of FIG. 2, it should be noted that it is portrayed in a partially cutaway manner with the right side of the stern bracket 14 removed (the right side looking forward (toward the boat or hull 12)).

As illustrated in FIG. 3, the power tilt-trim unit 44 is equipped with one hydraulic cylinder 442 for tilt angle regulation (hereinafter called the "tilt hydraulic cylinder") and, constituted integrally therewith, two hydraulic cylinders 444 for trim angle regulation (hereinafter called the "trim hydraulic cylinders"; only one shown).

As shown in FIG. 3, one end of the tilt hydraulic cylinder 442 is fastened to the stem bracket 14 and through it to the boat 12 and the other end (piston rod) thereof is fastened to a swivel case 50. One end of each trim hydraulic cylinder 444 is fastened to the stem bracket 14 and through it to the boat 12, similarly to the one end of the tilt hydraulic cylinder 442, and the other end (piston rod) thereof abuts on the swivel case 50.

The swivel case 50 is connected to the stem bracket 14 through a tilting shaft 52 to be relatively displaceable about the tilting shaft 52. A swivel shaft 54 is rotatably accommodated inside the swivel case 50. The swivel shaft 54 has its upper end fastened to a mount frame 56 and its lower end fastened to a lower mount center housing 58. The mount frame 56 and lower mount center housing 58 are fastened to an under cover 60 and an extension case 62 (more exactly, to mounts covered by these members).

The electric motor 38 (for steering) and a gearbox (gear mechanism) 66 for reducing the output of the electric motor 38 are fastened to an upper portion 50A of the swivel case 50. The gearbox 66 is connected to the output shaft of the electric motor 38 at its input side and is connected to the mount frame 56 at its output side. To be more specific, horizontal steering of the outboard motor 10 is thus power-assisted using the rotational output of the electric motor 38 to swivel the mount frame 56 and thus turn the propeller 22 and rudder 24.

As shown in the figure, the engine 16 is installed at the upper portion of the under cover 60 and the engine cover 18 is fastened thereon to cover the engine 16. The engine 16 has a throttle body 70 that is placed at a front position (at a position close to the hull or boat 12) inside the engine cover 18. Sucked air flows through the throttle body 70 and an intake manifold 68, and is drawn into cylinders (not shown).

The throttle body 70 is integrally connected with the electric motor (for throttle) 40 in such a way that the motor 40 is connected to a throttle shaft 70S (that supports a throttle valve 70V) via a gear mechanism (not shown) provided close to the throttle body 70.

The output of the engine 16 is transmitted to a propeller shaft 84 (housed in a gear case 82) through the crankshaft (not shown) and a driveshaft 80, to rotate the propeller 22. The aforesaid rudder 24 is integrally formed on the gear case 82. A forward gear 86F and a reverse gear 86R are provided around the propeller shaft 84 and mesh with a drive gear 80a to be rotated in opposite directions. A clutch 88 is provided between the forward gear 86F and the reverse gear 86R to be rotated with the propeller shaft 84. By engaging the clutch 88 with the forward gear 86F or the reverse gear 86R through the operation of a shift rod 90 and a shift slider 94 that are driven or moved by the electric motor (for shift-changing) 42, the direction of propeller rotation is changed and the shift change is effected between the forward advancing and reverse advancing.

The engine 16 will now be explained with reference to FIG. 4.

Figure 4:
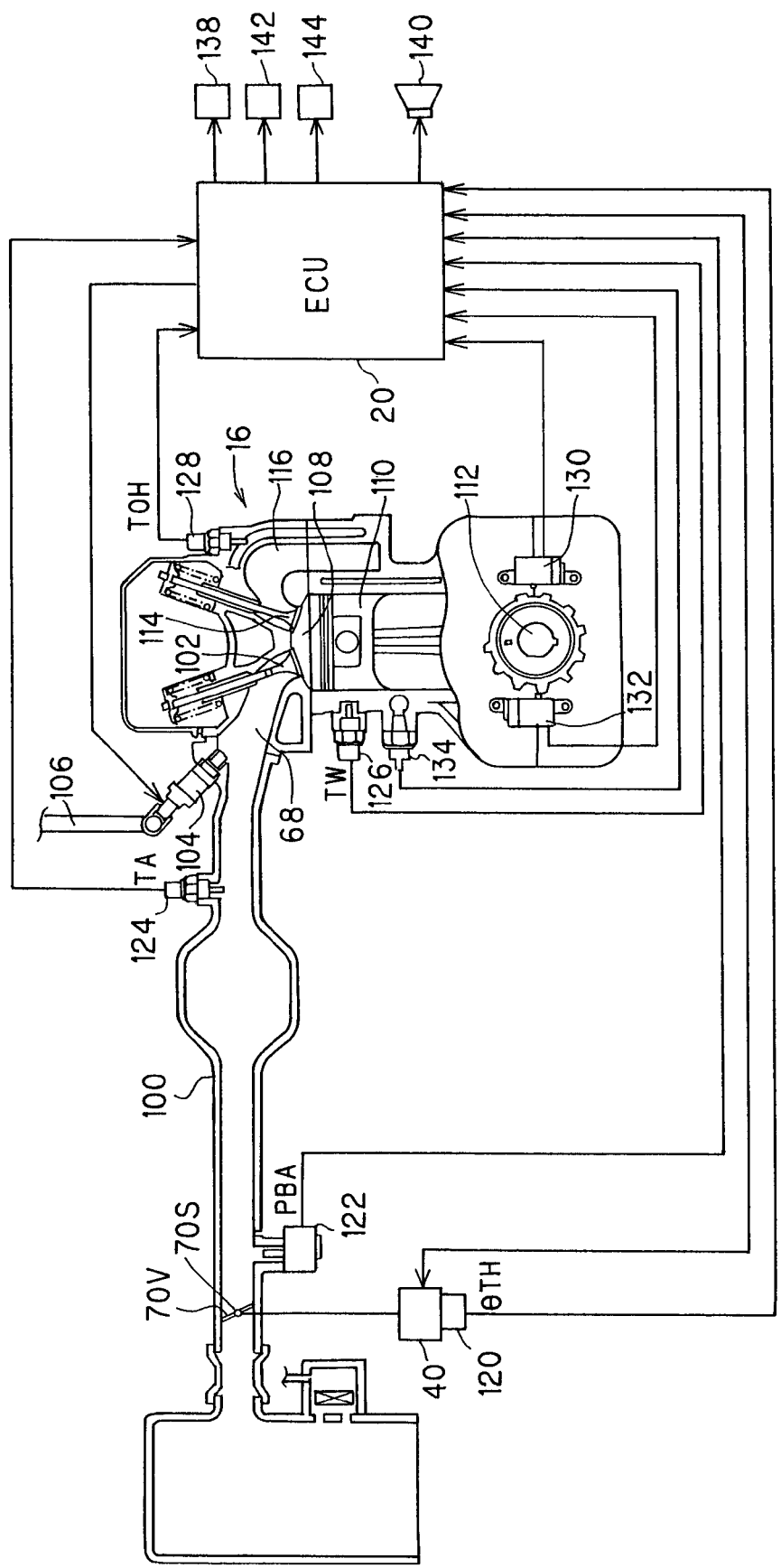
FIG. 4 is an overall schematic view of the engine installed in the outboard motor illustrated in FIG. 1.

As shown in FIG. 4, the engine 16 is equipped with an air intake pipe 100. Air drawn in through an air cleaner (not shown) is supplied to the intake manifolds 68 provided one for each of left and right cylinder banks (not shown), while the flow thereof is adjusted by the throttle valve 70V, and finally reaches an intake valves 102 of the respective cylinders (only one shown). A fuel injector 104 is installed in the vicinity of each intake valve 102 for injecting fuel (gasoline).

The fuel injector 104 is connected through a fuel pipe 106 to a fuel tank (not shown) containing gasoline. The fuel pipe 106 passes through a fuel pump (not shown) that pressurizes gasoline to be supplied to the fuel injector 104. The intake air is mixed with the injected gasoline to form an air-fuel mixture that flows into a combustion chamber 108 of each cylinder, where it is ignited by a spark plug (not shown) to bum explosively and drive down a piston 110. The so-produced engine output is taken out through a crankshaft 112. The exhaust gas produced by the combustion passes out through exhaust valves 114 into exhaust manifolds 70 (only one shown) provided one for each cylinder bank and is discharged to the exterior of the engine 16.

A throttle position sensor 120 is connected to the electric motor 40 and generates a signal proportional to the rotation of the motor 40 and indicative of the throttle opening θTH. A manifold absolute pressure sensor 122 is installed downstream of the throttle valve 70V and generates a signal indicative of the manifold absolute pressure PBA in the air intake pipe 100. In addition, an intake air temperature sensor 124 is installed downstream of the throttle valve 70V and generates a signal indicative of the intake air temperature TA.

A first temperature sensor 126 is installed in the water jacket (not shown) and generates a signal indicative of the engine coolant temperature TW, whilst a second temperature sensor 128 is installed in the vicinity of the exhaust manifolds 116 and generates a signal indicative of the engine temperature TOH.

A first pulser coil sensor 130 and a second pulser coil sensor 132 are installed in the vicinity of the crankshaft 112 and generates a cylinder discrimination signal, an angle signal indicative of the top dead center (TDC) of each piston and a crank angle signal once every 30 degrees.

An oil pressure (hydraulic) switch 134 is installed in the engine hydraulic circuit (not shown) and generates an OFF-signal when the oil pressure is greater than a predetermined value (i.e., when the amount of engine oil is sufficient), whilst it generates an ON-signal when the oil pressure is less than the predetermined value (when the amount of engine is insufficient)

These signals (outputs) of the sensors and switch are sent to the ECU 20. The ECU 20 detects or calculates the engine speed NE from the output of the first and second pulser coil sensors 130, 132. And it calculates a current command value from the output of the throttle lever position sensor 28S and outputs to the electric motor 40 through a driver (not shown) to drive the motor such that the throttle opening θTH is regulated as desired.

Moreover, the ECU 20 determines if the engine 16 overheats from the output of the second temperature sensor 128 and when the engine 16 is detected to be overheated, it turns on a warning lamp 138 and sounds a buzzer 140 to alert the operator. Similarly, the ECU 20 determines if the oil pressure is low (the amount of oil is insufficient) from the output of the oil pressure switch 134 and when the oil pressure is detected to be low, it turns on a warning lamp 142 and sounds the buzzer 140. At that time, if the engine speed is detected to be greater than a predetermined speed, it also turns on a warning lamp 144 and sounds the buzzer, as will be explained later.

The operation of the engine speed control system for outboard motors, more specifically the operation of the system when the occurrence of engine trouble is detected will then be explained.

Figure 5:
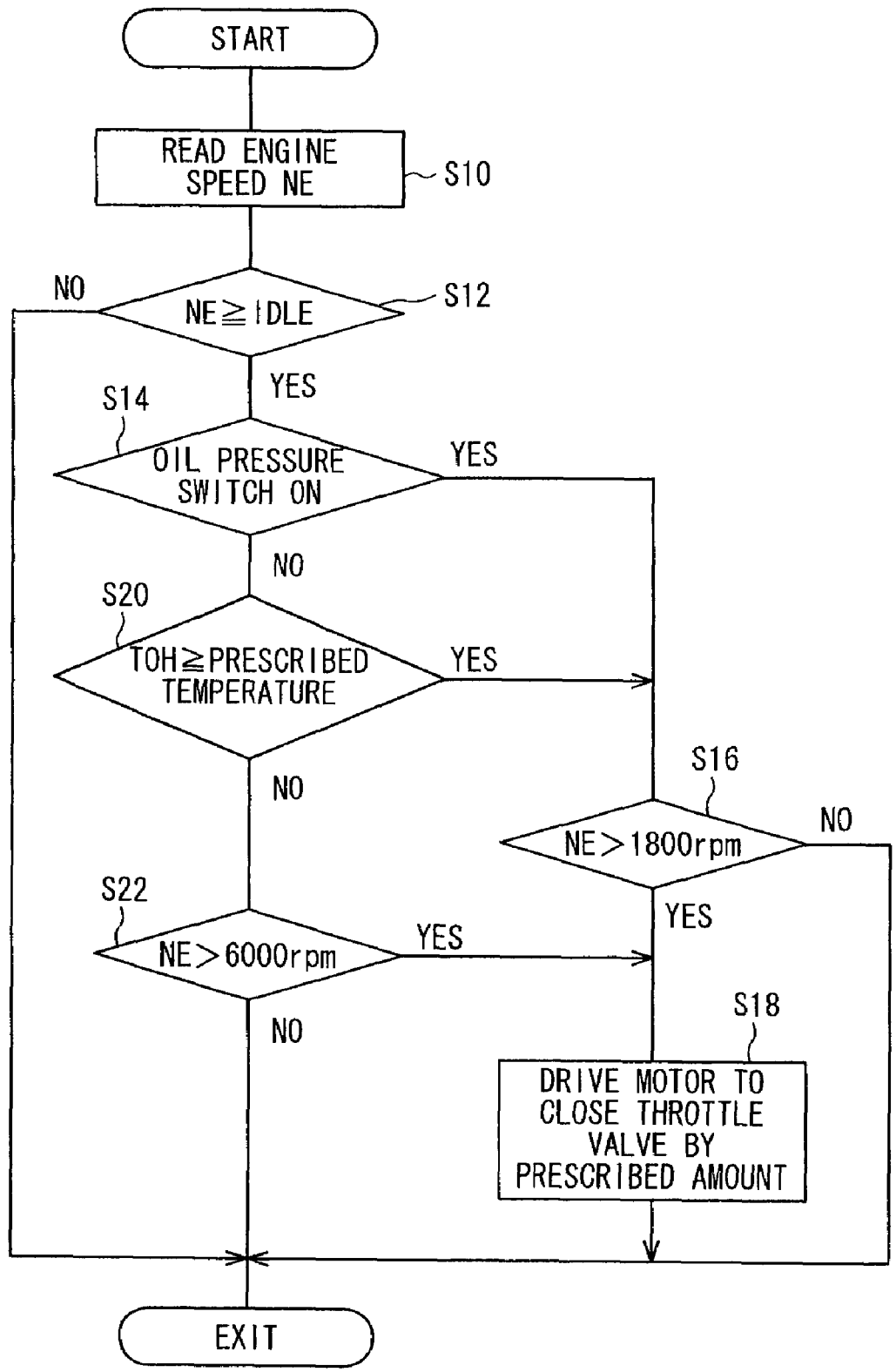
FIG. 5 is a flow chart showing the operation of the system illustrated in FIG. 1.

FIG. 5 is a flow chart showing the operation of the system. The program illustrated there is executed once every 100 msec.

The program begins in S10 in which the engine speed NE (detected from the outputs of the first and second pulser coil sensor 130, 132) is read, and the program proceeds to S12 in which it is determined whether the detected engine speed NE is equal to or greater than an idling speed (e.g., 500 rpm).

When the result is affirmative, the program proceeds to S14 in which it is determined whether the oil pressure switch 134 is on, i.e., it generates the ON-signal. In other words, it is determined whether the oil pressure is insufficient due to the shortage of engine (lubricant) oil. When the result is affirmative, the program proceeds to S16 in which it is discriminated whether the engine speed NE is greater than the aforesaid predetermined speed. This predetermined speed is set to an engine speed at which the engine 16 can assumably continue to run without causing a sudden failure or stop until the boat 12 has returned to port. This speed is set to be 1800 rpm, for example.

When the result is affirmative, the program proceeds to S18 in n which the throttle valve is closed by a prescribed mount (i.e., the throttle opening θTH is decreased by the prescribed amount). Specifically, the electric motor 40 is driven to move the throttle valve 70V in the closing direction by 0.1 degree such that the engine speed NE drops. At the same time, the warning lamp 142 is turned on and the buzzer 140 is sounded to alert the operator to the trouble. On the other hand, when the result in S16 is negative, the program skips S18 and is immediately terminated.

Explaining this, since it is determined or detected in S14 that the oil pressure is insufficient, it becomes necessary to stop and protect the engine 16 from being damaged. However, when an engine trouble occurs on the sea, the engine must still continue to run until the boat 12 has returned to port. For that reason, it is discriminated whether the engine speed exceeds the predetermined speed and if it does, the throttle opening θTH is decreased by the small amount (0.1 degree) each time the program is looped in such a manner that the engine speed NE is gradually lowered to the predetermined speed.

In other words, the system controls the engine speed NE at or below the predetermined speed so as to protect the engine 16 from being damaged, while avoiding stopping of the engine 16 such that the boat 12 can return to port even if such a trouble has occurred on the sea. At that instant, since the engine speed is gradually lowered, not by retarding ignition timing or thinning out ignitions, but by closing the throttle valve 70V little by little, the engine 16 does not vibrate and the operator is prevented from experiencing unpleasant feeling.

In conventional outboard motors, the throttle valve is mechanically connected to the throttle lever by a cable or the like in such a way that the operator's lever manipulation is immediately transmitted to the throttle valve. In order to drop the engine speed, this structure requires engine output reduction by retarding ignition timing or thinning out ignitions, thereby causing the engine to vibrate. On the other hand, in the system according to the embodiment, since the throttle valve 70V is driven or moved by the electric motor (actuator) 40, the amount of intake air can be decreased as desired irrespectively of the operator's throttle lever manipulation, when the occurrence of engine trouble is detected. With this, the system can decrease the engine speed NE smooth, without causing the engine 16 to vibrate.

Returning to the explanation of the flow chart of FIG. 5, when the result in S14 is negative, the program proceeds to S20 in which it is determined whether the engine temperature TOH (detected by the second temperature sensor 128) is greater than or equal to a prescribed temperature (e.g., 100° C.).

When the result is affirmative, since this indicates that engine 16 overheats, the program proceeds to S16 in which it is determined whether the engine speed NE exceeds the predetermined and if it does, the program proceeds to S18 in which the throttle value is closed by the amount and warning to the operator is made in the manner mentioned above.

On the other hand, when the result in S20 is negative, the program proceeds to S22 in which it is determined whether the engine speed NE exceeds a prescribed speed such as 6000 rpm. When the result is affirmative, since this indicates that the engine 16 revs excessively, the program proceeds to S18 in which the throttle value is closed by the amount and warning to the operator is made in the manner mentioned above. When the result in S22 is negative, the program is terminated.

When the result in S12 is negative, since it is not possible to further lower the engine speed, the program is immediately terminated.

In the system according to the embodiment, the throttle valve 70V is thus moved by the electric motor 40, and if the engine speed NE at the time of occurrence of engine trouble exceeds the predetermined speed (e.g., 1800 rpm), the motor 40 is driven to close the throttle valve 70V little by little (e.g., 0.1 degree) such that the engine speed NE drops gradually. With this, it becomes possible to protect the engine 16 from being damaged by the moderate engine speed reduction. And, since the engine speed is reduced by closing the throttle valve 70V to decrease the amount of intake air, no vibration occurs in the engine 16 and the operator does not experience unpleasant feeling.

Further, since it is configured that a trouble of the engine 16 includes at least one of engine overheating, shortage of engine oil (insufficient oil pressure) and excessive engine revving, and since the engine speed is reduced when any one of the above happens, the engine 16 can be firmly protected from being damaged.

As mentioned above, the embodiment is thus configured to have a system for controlling a speed of an internal combustion engine 16 installed in an outboard motor 10 mounted on a stern of a boat 12 and having a propeller 22 with a rudder 24 that is powered by the engine to propel the boat, the engine having a throttle valve 70V that regulates air to be sucked, comprising: an actuator (electric motor 40) connected to the throttle valve to move it in an opening direction or in a closing direction; engine speed detecting means (first and second pulser coil sensors 130, 132, ECU 20, S10) for detecting the speed of the engine NE; engine trouble detecting means for detecting a trouble occurred in the engine (ECU 20, S14, S20, S22); engine speed discriminating means (ECU 20, S16) for discriminating whether the detected engine speed NE exceeds a predetermined speed; and actuator driving means (ECU 20, S16) for driving the actuator to move the throttle valve in the closing direction such that the engine speed drops, when it is discriminated that the detected engine speed exceeds the predetermined speed.

In the system, the trouble includes at least one of engine overheating (S20), shortage of engine oil (S14) and excessive engine revving (S22).

The system further includes alerting means (warning lamp 142, buzzer 140, ECU 20, S16) for alerting an operator to occurrence of trouble.

In the system, the predetermined speed is a speed at which the engine can assumably continue to run such that the boat 12 returns to port.

The actuator driving means drives the actuator to move the throttle valve in the closing direction by an amount repeatedly (i.e., at every interval of e.g., 100 msec) such that the engine speed drops gradually.

It should be noted in the above, although the electric motor (for throttle) 40 is configured to be a DC motor, it may be other motor such as a stepper motor.

The entire disclosure of Japanese Patent Application No. 2002-289942 filed on Oct. 2, 2002, including specification, claims, drawings and summary, is incorporated herein in its entirety.

While the invention has thus been shown and described with reference to specific embodiments, it should be noted that the invention is in no way limited to the details of the described arrangements; changes and modifications may be made without departing from the scope of the appended claims.

What is claimed is:

1. A system for controlling a speed of an internal combustion engine installed in an outboard motor mounted on a boat and having a propeller powered by the engine to propel the boat, the engine having a throttle valve that regulates air to be sucked, comprising:
    an actuator connected to the throttle valve to move it in an opening direction or in a closing direction;
    engine speed detecting means for detecting the speed of the engine;
    engine trouble detecting means for detecting a trouble occurred in the engine;
    engine speed discriminating means for discriminating whether the detected engine speed exceeds a predetermined speed which is larger than an engine idle speed when it is detected that the trouble has occurred in the engine; and
    actuator driving means for driving the actuator to move the throttle valve in the closing direction such that the engine speed drops, when it is discriminated that the detected engine speed exceeds the predetermined speed, wherein
    the actuator driving means drives the actuator to move the throttle valve in the closing direction by an amount repeatedly such that the engine speed is gradually lowered to the predetermined speed.

2. A system according to claim 1, wherein the trouble includes at least one of engine overheating, shortage of engine oil and excessive engine revving.

3. A system according to claim 1, further including:
    alerting means for alerting an operator to occurrence of the trouble.

4. A system according to claim 1, wherein the predetermined speed is a speed at which the engine can assumably continue to run until the boat has returned to port.

5. A method of controlling speed of an internal combustion engine installed in an outboard motor mounted on a boat and having a propeller powered by the engine to propel the boat, the engine having a throttle valve that regulates air to be sucked and an actuator connected to the throttle valve to move it in an opening direction or in a closing direction, comprising the steps of:
    detecting the speed of the engine;
    detecting a trouble occurred in the engine;
    discriminating whether the detected engine speed exceeds a predetermined speed which is larger than an engine idle speed when it is detected that the trouble has occurred in the engine; and
    driving the actuator to move the throttle valve in the closing direction such that the engine speed drops, when it is discriminated that the detected engine speed exceeds the predetermined speed, wherein
    the step of actuator driving drives the actuator to move the throttle valve in the closing direction by an amount repeatedly such that the engine speed is gradually lowered to the predetermined speed.

6. A method according to claim 5, wherein the trouble includes at least one of engine overheating, shortage of engine oil and excessive engine revving.

7. A method according to claim 5, further including the step of:
    alerting an operator to occurrence of the trouble.

8. A method according to claim 5, wherein the predetermined speed is a speed at which the engine can assumably continue to run until the boat has returned to port.

9. A computer program embodied on a computer-readable medium for controlling speed of an internal combustion engine installed in an outboard motor mounted on a boat and having a propeller powered by the engine to propel the boat, the engine having a throttle valve that regulates air to be sucked and an actuator connected to the throttle valve to move it in an opening direction or in a closing direction, comprising the steps of:
    detecting the speed of the engine;
    detecting a trouble occurred in the engine;
    discriminating whether the detected engine speed exceeds a predetermined speed which is larger than an engine idle speed when it is detected that the trouble has occurred in the engine; and
    driving the actuator to move the throttle valve in the closing direction by an amount repeatedly such that the engine speed is gradually lowered to the predetermined speed, when it is discriminated that the detected engine speed exceeds the predetermined speed.

* * * * *